(12) United States Patent
Morrow et al.

(10) Patent No.: US 9,340,739 B1
(45) Date of Patent: May 17, 2016

(54) ENHANCED LANDFILL GAS TREATMENT

(71) Applicants: David C. Morrow, Midland, TX (US);
Paul D. Morrow, Midland, TX (US);
Luke N. Morrow, Midland, TX (US)

(72) Inventors: David C. Morrow, Midland, TX (US);
Paul D. Morrow, Midland, TX (US);
Luke N. Morrow, Midland, TX (US)

( * ) Notice: Subject to any disclaimer, the term of this patent is extended or adjusted under 35 U.S.C. 154(b) by 2 days.

(21) Appl. No.: 14/458,128

(22) Filed: Aug. 12, 2014

Related U.S. Application Data

(63) Continuation-in-part of application No. 13/199,596, filed on Sep. 2, 2011, now Pat. No. 8,840,708.

(51) Int. Cl.
*B01D 53/14* (2006.01)
*C10L 3/10* (2006.01)
*B01D 19/00* (2006.01)

(52) U.S. Cl.
CPC .............. *C10L 3/104* (2013.01); *B01D 53/1406* (2013.01); *B01D 53/1425* (2013.01); *B01D 53/1475* (2013.01); *B01D 19/0036* (2013.01)

(58) Field of Classification Search
None
See application file for complete search history.

(56) References Cited

U.S. PATENT DOCUMENTS

| | | | | |
|---|---|---|---|---|
| 3,121,624 A * | 2/1964 | Matsch | ................... | B01D 53/14 95/175 |
| 4,710,211 A * | 12/1987 | Gazzi | ................. | B01D 53/1406 62/634 |
| 7,604,684 B2 * | 10/2009 | Menzel | ............. | B01D 53/1406 95/173 |
| 7,699,914 B1 * | 4/2010 | Morrow | ............. | B01D 53/1406 95/172 |
| 7,967,896 B2 * | 6/2011 | Lechnick | ........... | B01D 53/1425 95/172 |
| 8,211,213 B2 * | 7/2012 | Lechnick | .................. | C01B 3/52 95/159 |
| 8,282,899 B2 * | 10/2012 | Bahr | .................. | B01D 53/1487 423/220 |
| 8,518,155 B2 * | 8/2013 | Palamara | ........... | B01D 19/0036 95/163 |
| 8,540,803 B2 * | 9/2013 | Menzel | ............. | B01D 53/1425 95/173 |
| 8,696,798 B2 * | 4/2014 | Mak | .................... | B01D 53/1425 95/172 |
| 2009/0241778 A1 * | 10/2009 | Lechnick | ........... | B01D 53/1425 95/177 |
| 2011/0072969 A1 * | 3/2011 | Lechnick | ........... | B01D 53/1418 95/199 |

* cited by examiner

*Primary Examiner* — Duane Smith
*Assistant Examiner* — Phillip Shao
(74) *Attorney, Agent, or Firm* — www.bobharter.com; Robert J. Harter

(57) ABSTRACT

A method for recovering methane gas from a landfill involves the use of a main absorber, a flash system, an optional ancillary absorber and an optional polishing absorber. The recovered gas is maintained at a temperature that enhances a solvent's ability to absorb carbon dioxide from the recovered gas. While the main absorber uses the solvent for absorbing most of the carbon dioxide from the recovered gas, the flash system removes much of the carbon dioxide from the solvent exiting the main absorber. In some examples, at least portion of the flash system operates at subatmospheric pressure to create a vacuum that draws in a generally inert stripper gas (e.g., air, nitrogen, etc.) at atmospheric pressure. The stripper gas helps remove carbon dioxide from the solvent in the flash system.

7 Claims, 7 Drawing Sheets

ENHANCED LANDFILL GAS TREATMENT

CROSS REFERENCE TO RELATED APPLICATIONS

This application is a Continuation-In-Part of co-pending patent application Ser. No. 13/199,596 filed on Sep. 2, 2011 by the present inventor.

FIELD OF THE DISCLOSURE

The subject invention generally pertains to processing landfill gas and more specifically to an absorption system and method for recovering and purifying methane gas.

BACKGROUND

Decomposing garbage buried in a landfill can generate landfill gas that can be extracted and processed to provide methane gas of varying degrees of purity and energy content. Processing plants have been developed for recovering and purifying methane gas, but there continues to be a need for better systems and methods.

DETAILED DESCRIPTION

Figure 1:
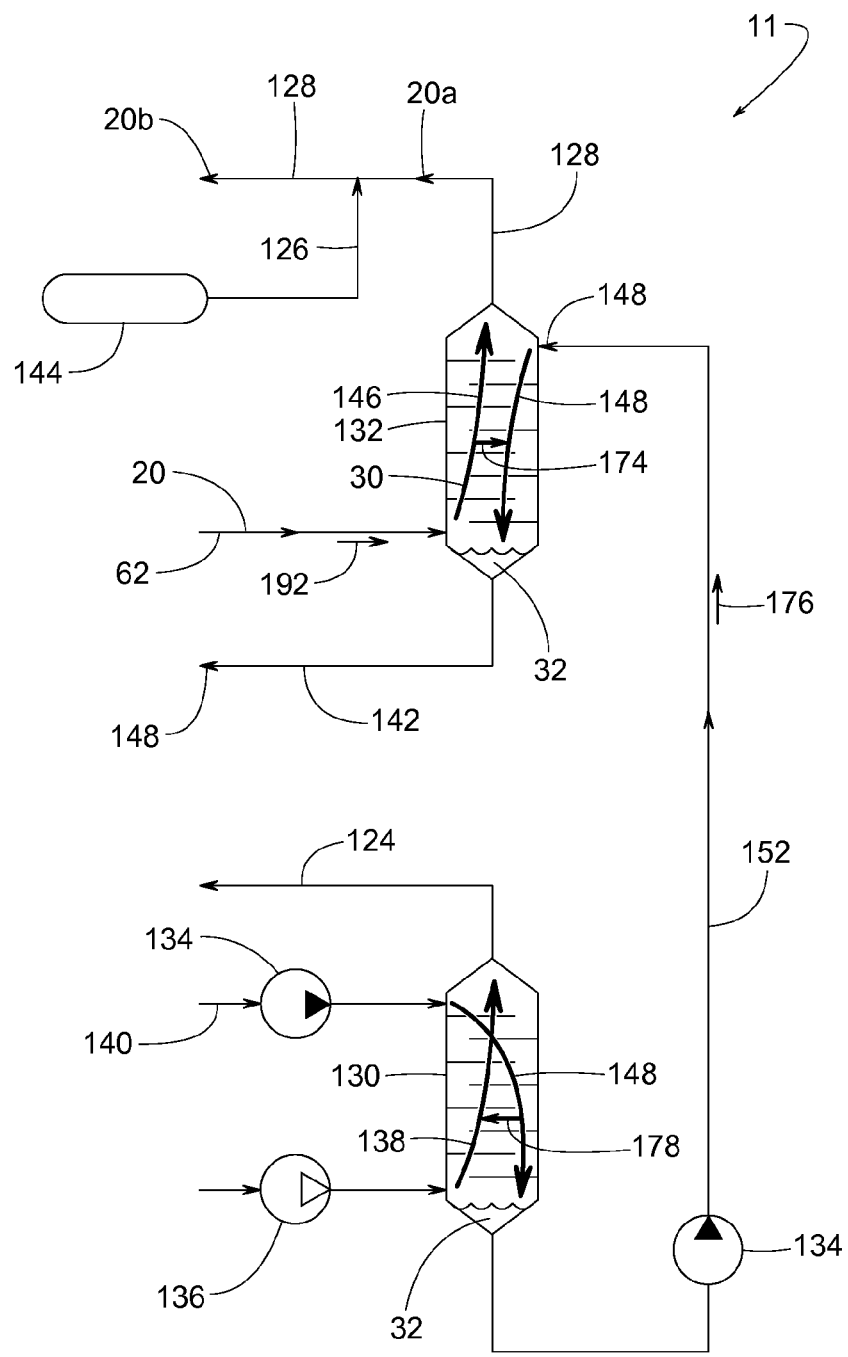
FIG. 1 is a schematic view of an example absorption system and method.

FIG. 1 shows an example absorption system 11 for improving the gas purifying operation of various methane gas processing systems. Examples of such gas processing systems include, but are not limited to, a triple-effect absorption system 10a, shown in FIG. 2, and an absorption system 10b, shown in FIG. 3. To understand the purpose and function of absorption system 11, the structure and operation of systems 10a and 10b will be explained first.

Figure 2:
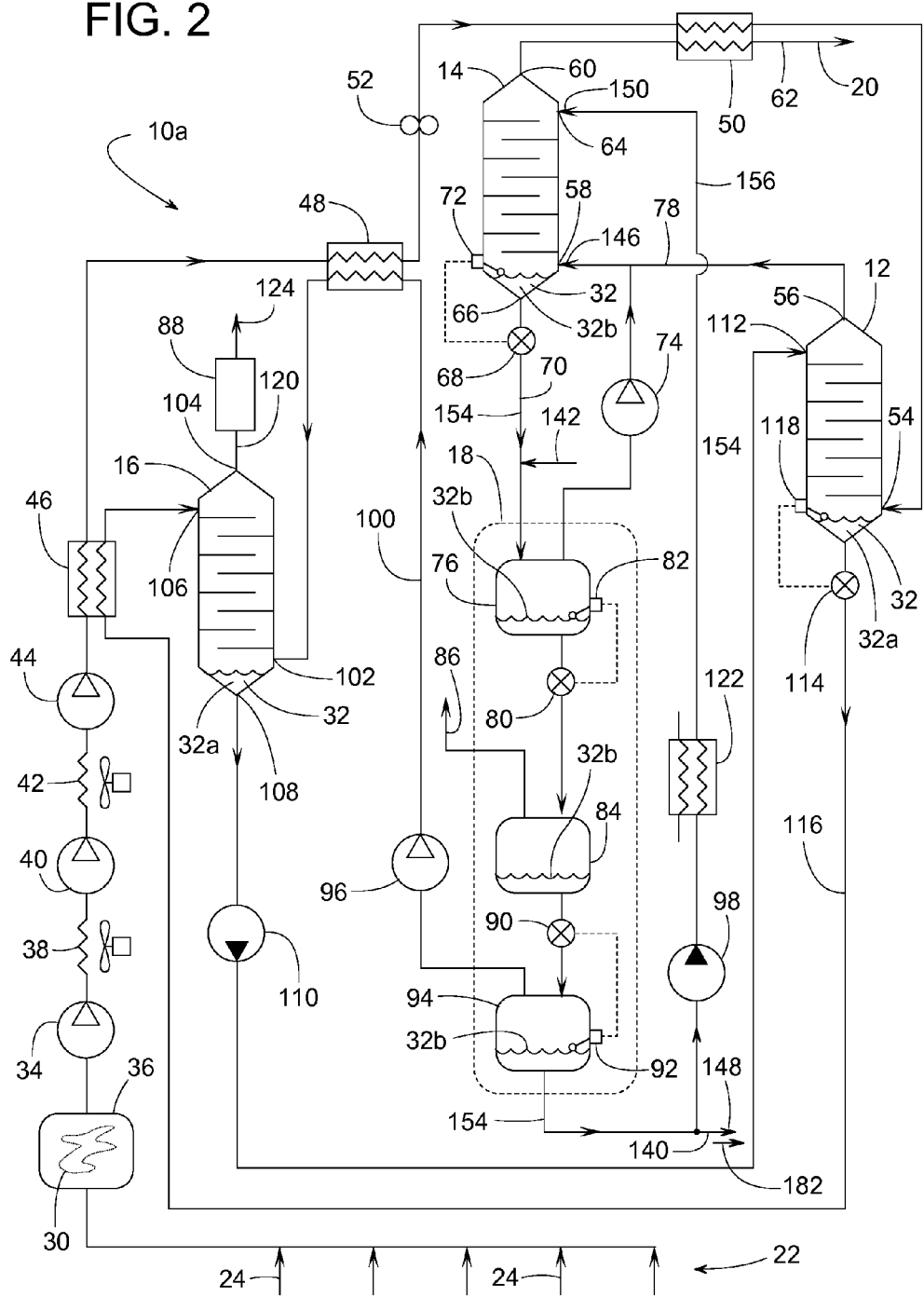
FIG. 2 a schematic view of an example absorption system connectable to the system shown in FIG. 1.

Referring to FIG. 2, triple-effect absorption system 10a includes a first absorber 12, a second absorber 14, a third absorber 16, plus a flash system 18 that work together to recover relatively clean methane gas 20 from a landfill 22. Landfill 22 is a large field of buried garbage with a series of wells 24 that tap a landfill gas 30 generated by the decomposing garbage. Landfill gas 30 may be comprised of methane contaminated with various impurities such as $CO_2$ (carbon dioxide), air, hydrocarbons, $H_2S$ (hydrogen sulfide), aromatics and water. Each impurity's concentration may vary from its initial level in the landfill down to zero as gas 30 is progressively processed through system 10a.

To recover and separate the methane from its contaminants, a solvent 32 having an affinity for contaminants is circulated through absorbers 12, 14 and 16. In first absorber 12, solvent 32 absorbs trace contaminants of hydrocarbons, aromatics and water from landfill gas 30. In second absorber 14, solvent 32 absorbs $CO_2$ from gas 30. And in third absorber 16, $CO_2$ absorbs trace contaminants from solvent 32. Solvent 32 represents any chemical that can absorb and subsequently release one or more impurities that can contaminate methane gas. Examples of solvent 32 include, but are not limited to, SELEXOL (registered trademark of Union Carbide Chemicals & Plastics Technology Corporation of The Dow Chemical Company) and DEPG (diethylpropylene glycol). System 10a has two charges of solvent 32. A first portion 32a of solvent 32 circulates between absorbers 12 and 16, and a second portion 32b of solvent 32 circulates between absorber 14 and flash system 18.

In operation, a blower 34 draws landfill gas 30 up from within wells 24 into a collection tank 36. Blower 34 operates at an absolute suction pressure of about 10 to 60 inch water vacuum (subatmospheric pressure) and a discharge pressure of about 3 psig. A cooler 38 reduces the temperature of gas 30 from about 160° F. to about 120° F. A screw compressor 40 takes the temperature and pressure of gas 30 to about 230° F. and 85 psig. A cooler 42 reduces the temperature of gas 30 to about 120° F. A reciprocating compressor 44 increases the pressure of gas 30 to about 450 psig. In the example of FIG. 2, a solvent heat exchanger 46, a $CO_2$ heat exchanger 48, and a methane heat exchanger 50 each extracts heat from compressed gas 30 to enhance the effectiveness of system 10a. In the examples shown in FIGS. 5-7, an air cooler 47 cools the compressed gas 30 to about 120° F. In some examples, a conventional sulfur treater 52 is used to help extract at least some hydrogen sulfide and mercaptan compounds from gas 30.

In the example of FIG. 2, gas 30 enters a lower gas inlet 54 of absorber 12 at about 120° F. and 450 psig, travels upward through absorber 12, and exits through an upper gas outlet 56 of absorber 12 at about 450 psig. As gas 30 travels through first absorber 12, first solvent portion 32a travels downward in intimate contact with gas 30 to absorb trace contaminants from gas 30. With most or at least some of the trace contaminants removed, gas 30 enters a lower gas inlet 58 of second absorber 14 at about 125° F. and 450 psig. Gas 30 leaving absorber 12 is comprised of about 42 mol % $CO_2$. It should be noted that the term, "mol %," as used throughout this patent, means molar percent, which is the ratio of the moles of a substance in a mixture to the total moles of the mixture with the ratio being multiplied by a hundred, i.e., mol % represents the number of moles of a substance in a mixture as a percentage of the total number of moles in the mixture. The term, "concentration," as used throughout this patent, is expressed in terms of mol %.

To remove $CO_2$ from gas 30, the gas travels upward from lower gas inlet 58 to an upper gas outlet 60 to release the $CO_2$ to second solvent portion 32b, which travels downward in intimate, $CO_2$-absorbing contact with gas 30. With most of the $CO_2$ now removed from gas 30, the gas is conveyed to a supply line 62 where the treated gas 20 is available for further processing. Prior to reaching supply line 62, however, gas 20 leaving second absorber 14 first passes through heat exchanger 50 to precool gas 30 that is about to enter lower gas inlet 54 of first absorber 12.

Second solvent portion 32b, which absorbs $CO_2$ from gas 30 in second absorber 14, travels downward from an upper liquid inlet 64 to collect just above a lower liquid outlet 66. The second solvent portion 32b is at about 50 to 55° F. A control valve 68 in a solvent line 70 (second solvent line) responds to a liquid level sensor 72 to maintain a predetermined head of liquid solvent 32b at the bottom of second absorber 14. Valve 68 controllably releases solvent 32b at about 450 psig in second absorber 14 to first flash tank 76 at about 250 psig. The lower pressure in first flash tank 76 causes some $CO_2$ to be released from the second solvent portion 32b. Compressor 74 returns this $CO_2$ along with some methane to a gas line 78 to mix with gas 30 from first absorber 12. Together, gas line 78 and compressor 74 feed second absorber 14 with gas 30 that is about 45 mol % $CO_2$.

The second solvent portion 32b pools at the bottom of first flash tank 76. A control valve 80 (first control valve) responsive to a liquid level sensor 82 controls the liquid level in first flash tank 76 and controllably feeds second solvent portion 32b into a second flash tank 84, which is slightly above atmospheric pressure. The pressure drop from flash tank 76 to flash tank 84 causes more $CO_2$ to escape from the second solvent portion 32b. That $CO_2$ is surplus, as it is not needed for stripping trace contaminants from the first solvent portion 32a in third absorber 16, thus that portion of the $CO_2$ can be vented directly, or through a carbon filter, to atmosphere via a vent line 86. If that $CO_2$ were not vented to atmosphere but instead directed into third absorber 16, the surplus $CO_2$ would create an unnecessary incineration load on an incinerator 88, which will be explained later.

Another control valve 90 (second control valve) responsive to a liquid level sensor 92 in a downstream third flash vessel 94 controls the liquid level in third flash tank 94 and controllably feeds the second solvent portion 32b into third flash tank 94. A compressor 96 maintains third flash tank 94 at about a 4 to 5 psia (negative gage pressure of about −9 to −10 psig), which cause additional $CO_2$ to escape from the second solvent portion 32b. This additional $CO_2$ is later used in third absorber 16 to remove the trace contaminants from first solvent portion 32a. A pump 98 draws the liquid second portion 32b of solvent 32 from the bottom of flash tank 94 and returns it to upper liquid inlet 60 of second absorber 14 to drive the solvent cycle of second absorber 14 and flash system 18.

To strip the trace contaminants from the first portion 32a of solvent 32, compressor 96 draws $CO_2$ from third flash tank 94, and a $CO_2$ line 100 and heat exchanger 48 convey the $CO_2$ into a lower gas inlet 102 of third absorber 16. Vent line 86 represent a first flow path, and $CO_2$ line 100 represents a second flow path for the $CO_2$. With two flow paths, only a minimal amount of $CO_2$ is used for stripping trace contaminants from first portion 32a of solvent 32 in third absorber 16, and surplus $CO_2$ can be vented directly to atmosphere.

In some examples, as shown in FIG. 2, heat exchanger 48 heats the $CO_2$ before the $CO_2$ enters third absorber 16. Once inside third absorber 16, the $CO_2$ travels upward to an upper gas outlet 104. At the same time, the first solvent portion 32a with absorbed trace contaminants travels from an upper liquid inlet 106 in third absorber 16 down to a lower liquid outlet 108. As this first solvent portion 32a and the $CO_2$ travel in intimate contact with each other inside third absorber 16, the $CO_2$ strips contaminants from the first solvent portion 32a.

The resulting relatively uncontaminated first solvent portion 32a collects at the bottom of third absorber 16. A pump 110 returns the clean first solvent portion 32a to an upper gas inlet 112 of absorber 12 so that the first solvent portion 32a can absorb additional trace contaminants from the incoming landfill gas 30.

To maintain first solvent portion 32a at a certain liquid level at the bottom of first absorber 12, a control valve 114 in a first solvent line 116 responds to a liquid level sensor 118, thereby controlling the delivery of first solvent portion 32a to third absorber 16 and maintaining a predetermined pressure differential between absorbers 12 and 16. The pressure differential is about 450 psig and it is that pressure that forces first solvent portion 32a to upper liquid inlet 106 of third absorber 16.

Before entering third absorber 16, first solvent portion 32a is heated by gas 30 within heat exchanger 46. Heating first solvent portion 32a enables the $CO_2$ in third absorber 16 to more readily strip the trace contaminants from the first solvent portion 32a, thus less $CO_2$ is needed for absorbing the contaminants.

After absorbing the trace contaminants from first solvent portion 32a, the $CO_2$ and trace contaminants exhaust out through an upper gas outlet 120 of third absorber 16 and enter incinerator 88. Using the trace contaminants and treated gas 20 as fuel, incinerator 88 heats the $CO_2$ (from $CO_2$ line 100) to at least 1400° F. before exhausting the $CO_2$ and the resulting combustion products to atmosphere 124. By venting a portion of the $CO_2$ through vent line 86, as opposed to directing all of the $CO_2$ into third absorber 16, less energy is needed to heat the contaminated $CO_2$ to 1400° F., thus the trace contaminants can provide all or at least most of the necessary combustion energy.

To effectively strip $CO_2$ from the second solvent portion 32b and supply third absorber 16 with a sufficient amount of $CO_2$ to thoroughly strip the first solvent portion 32a of its absorbed trace contaminants yet limit the amount of $CO_2$ delivered to third absorber 16 so as not to extinguish or dampen the combustion within incinerator 88, the relative fluid flow rates, temperatures and pressures of system 10a need to be properly balanced. In some examples, the pressure in first absorber 12 is nearly equal to or at least within 10% of the pressure in second absorber 14, the pressure in first absorber 12 and second absorber 14 are much greater than and preferably over five times as great as the pressure in third absorber 16, the flow rate of solvent 32 in first absorber 12 and third absorber 16 are substantially equal or at least within 10% of each other, the flow rate of solvent 32 through second absorber 14 is much greater than and preferably at least ten times as great as the flow rate of solvent through first absorber 12, and the flow rate of solvent 32 through second absorber 14 is much greater than and preferably at least ten times as great as the flow rate of solvent through third absorber 16. In some cases, the first solvent portion 32a flows at about 10 gpm, and the second solvent portion 32b flows at about 210 gpm.

The pressure inside first absorber 12 is approximately 450 psig, thus the pressure of gas 30 inside first absorber 12 and the pressure of solvent 30 inside first absorber 12 are also at about 450 psig. The pressure inside second absorber 14 is approximately 450 psig, thus the pressure of gas 30 inside second absorber 14 and the pressure of solvent 30 inside second absorber 14 are also at about 450 psig. The pressure inside third absorber 16 is near zero psig, thus the pressure of gas 30 inside third absorber 16 and the pressure of solvent 30 inside third absorber 16 are also at about zero psig.

In some examples, a refrigerated or otherwise cooled heat exchanger 122 is added to cool the second solvent portion 32b circulated through second absorber 14. Such cooling increases the second portion's ability to absorb $CO_2$ inside second absorber 14. In some examples, the second solvent portion 32b entering second absorber 14 is naturally cooled to a temperature of about 40 to 50° F. As for the other heat exchangers of system 10a, the heat supplied to heat exchangers 46, 48 and 50 would otherwise be wasted heat created directly or indirectly by compressors 34, 40 and/or 44. It should be noted that any one or more of heat exchangers 38, 42, 46, 48, 50, and 122 may be optionally omitted.

Figure 3:
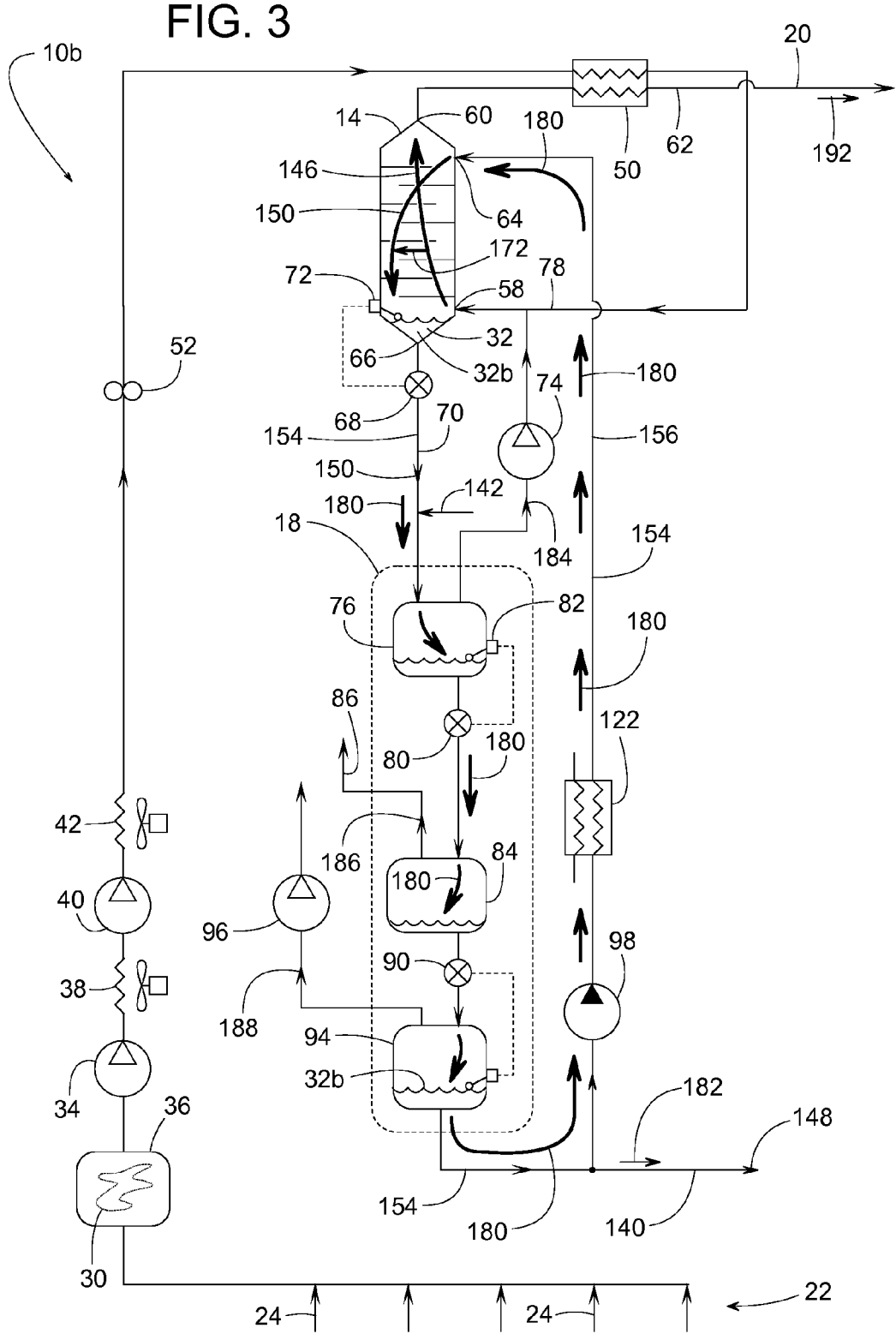
FIG. 3 is a schematic view of another example absorption system connectable to the system shown in FIG. 1.

In the example shown in FIG. 3, absorption system 10b is created by eliminating several components of system 10a. The eliminated items include absorbers 12 and 14 and their associated components (e.g., items 46, 48, 88, 110, 114, 116 and 118. Remaining portions of absorption system 10b, shown in FIG. 2, are retained to operate in a manner similar to that of system 10a, wherein supply line 62 makes treated gas 20 available for further processing.

Absorption system 11, of FIG. 1, can be added to systems 10a and 10b to improve the quality of methane gas 20. In some examples, gas 20 has a concentration of carbon dioxide of about 2 mol % (or slightly less or more), and system 11 can improve that to provide methane gas 20a with a carbon dioxide concentration of less than 1 mol % and perhaps as low as 0.4 to 0.8 mol %. In some examples, system 11 further improves the quality of gas 20a by injecting a gas with a higher energy content than that of methane. In some cases, for example, propane gas 126 with an energy content of about 2,500 BTU/scf is injected into a discharge line 128 to mix with methane gas 20a. While pure methane has an energy content of about 1,010 BTU/scf, methane gas 20a might have an energy content of less than 950 BTU/scf due to gas 20a having various contaminants, such as nitrogen and some carbon dioxide. Thus, system 11 minimizing the concentration of carbon dioxide in gas 20a and, in some examples, adding propane 126 provides high quality methane 20b having significantly less than 2 mol % of carbon dioxide and an energy content greater than 950 BTU/scf and in some cases greater than 970 BTU/scf.

In the example shown in FIG. 1, system 11 comprises an ancillary absorber 130, a polishing absorber 132, one or more pumps 134 pumping a portion 148 of solvent 32 (portion of solvent 148) through absorbers 130 and 132, an air supply 136 (or supply of nitrogen) forcing a current of air 138 (or current of nitrogen) through ancillary absorber 130, a line 140 conveying the portion of solvent 148 from one absorption system (e.g., system 10a or 10b) to system 11, a return line 142 for injecting the portion of solvent 148 back into the main absorption system (e.g., system 10a or 10b), and discharge line 128 for conveying gas 20a from polishing absorber 132. Examples of supply 136 include, but are not limited to, a blower, a fan, a compressor, a pressurized tank of nitrogen, etc. In some examples, ancillary absorber 130 and/or 132 includes or is associated with means for controlling the flow of solvent through absorber 130 and/or 132. Examples of such means include, but are not limited to, controlling the operation of one or more pumps 134 and/or the use of various flow control elements such as those used in system 10a of FIG. 2 (e.g., control valves 68, 80, 90, 114; and liquid level sensors 72, 82, 92 and 118). Item 144 schematically represents an optional source of propane 126, which normally requires a pump, for injection into gas 20a to produce gas 20b, wherein gas 20b has a higher energy content than that of gas 20a.

In some examples illustrated in FIG. 1, nitrogen is used instead of air, where in such examples, reference numeral 136 refers to a supply of nitrogen and numeral 138 refers to a current of nitrogen. The term "nitrogen" refers to a gas having an appreciably greater concentration of nitrogen than that of just air, e.g., such gas has a nitrogen concentration in excess of 80%. The term, "air" refers to the Earth's atmosphere that when dry is a mixture of approximately 78% nitrogen, 21% oxygen and 1% other gases (percentage values being with respect to volume). The term, "mostly air" refers to a gas mixture wherein at least half of its volume is comprised of 78% nitrogen, 21% oxygen and 1% other gases.

Connecting system 11 of FIG. 1 to system 10a of FIG. 2 or system 10b of FIG. 3 provides a combined absorption system comprising a main absorber (e.g., absorber 14), ancillary absorber 130, polishing absorber 132, flash system 18, and lines 140 and 142 connecting system 11 to system 10a or 10b. In the operation of combined systems 11 and 10a or 11 and 10b, a current of gas 146 (comprising gas 30) flows up through main absorber 14 from inlet 58 to outlet 60. From outlet 60, the current of gas 146 flows sequentially through line 62 to polishing absorber 132, up through polishing absorber 132, and out through discharge line 128 to be used or sold.

To remove carbon dioxide from gas 30, a main current of solvent 150 (comprising solvent 32) flows through main absorber 14 while in intimate contact with the current of gas 146. After the main current of solvent 150 absorbs carbon dioxide from current of gas 146, the main current of solvent 150 flows through flash system 18, which removes carbon dioxide from the main current of solvent 150. While pump 98 pumps most of the current of solvent 150 from the bottom of flash system 18 to inlet 64 of main absorber 14, pump 134 pumps a lesser portion of solvent 148 through line 140 to ancillary absorber 130 (FIG. 1). The portion of solvent 148 flows through ancillary absorber 130 in intimate contact with the current of air 138.

As the current of air 138 and the portion of solvent 148 flow through ancillary absorber 130, the current of air 138 extracts carbon dioxide from the portion of solvent 148. After air 138 removes carbon dioxide from the portion of solvent 148, air 138 is vented to atmosphere via a line 124, and a line 152 conveys the portion of solvent 148 to polishing absorber 132. As the portion of solvent 148 flows through polishing absorber 132, the current of gas 146 from line 62 flows up through polishing absorber 132 in intimate contact with the portion of solvent 148, whereby the portion of solvent 148 absorbs carbon dioxide from the current of gas 146. The current of gas 146 now becomes gas 20a and, in some examples, ultimately becomes gas 20b in cases where propane 126 is added to gas 20a. Gas 20a or 20b can be sold or used as needed.

As for the portion of solvent 148 after having flowed through polishing absorber 132, line 142 injects the portion of solvent 148 back into a main solvent loop 154, wherein main solvent loop 154 comprises main absorber 14, line 70, flash system 18, and a return line 156. In some examples, line 142 injects the portion of solvent 148 at a point between main absorber 14 and flash system 18 (e.g., at or downstream of absorber 14 and at or upstream of flash system 18 with respect to solvent flow). Once injected in main solvent loop 154, in some examples, the portion of solvent 148 becomes part of the main current of solvent 150.

Figure 4:
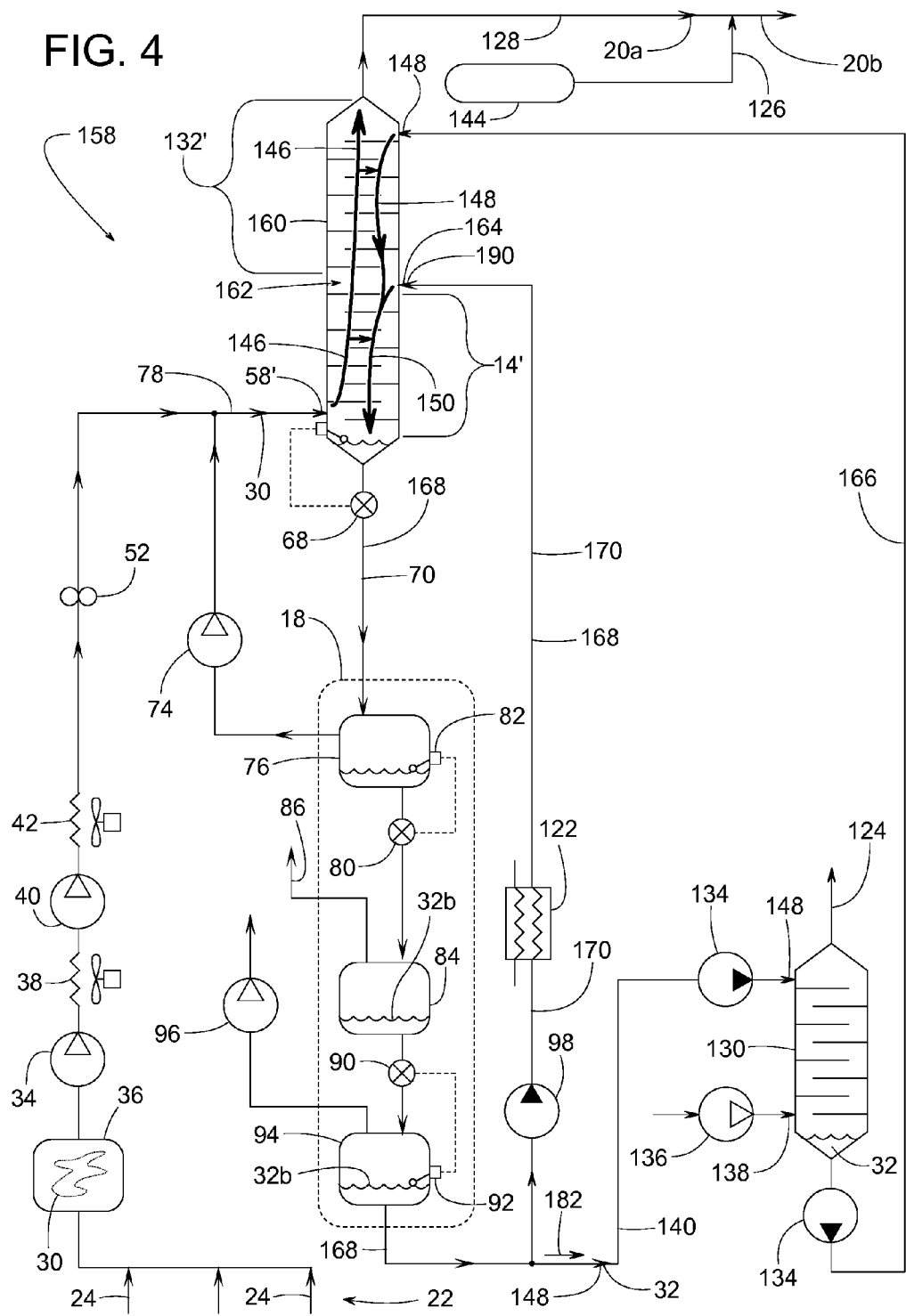
FIG. 4 is a schematic view of yet another example absorption system and method.

In some examples, as shown in FIG. 4, an absorption system 158 includes the combination of a main absorber 14' and a polishing absorber 132' that share a common outer shell 160 (i.e., absorbers 14' and 132' are combined in a single vessel). In this example, line 78 conveys gas 30 to an inlet 58' of main absorber 14'. From inlet 58', a current of gas 146 flows up through main absorber 14', through an area of transition 162 between main absorber 14' and polishing absorber 132', through polishing absorber 132', and out through discharge line 128.

To remove carbon dioxide from gas 146, a main current of solvent 150 flows through main absorber 14' while being in intimate contact with the current of gas 146. After the main current of solvent 150 absorbs carbon dioxide from the current of gas 146, the main current of solvent 150 flows through flash system 18, which removes carbon dioxide from the main current of solvent 150. Pump 98 pumps most of the main current of solvent 150 from the bottom of flash system 18 to an inlet 164 at the area of transition 162 between absorbers 14' and 132'. At least one pump 134 pumps a lesser portion of solvent 148 through line 140 to ancillary absorber 130. The portion of solvent 148 flows through ancillary absorber 130 in intimate contact with the current of air 138, basically in the manner as shown in FIG. 1.

As the current of air 138 and the portion of solvent 148 flow through ancillary absorber 130, the current of air 138 extracts carbon dioxide from the portion of solvent 148. After air 138 removes carbon dioxide from the portion of solvent 148, air 138 is vented to atmosphere via line 124, and a line 166 conveys the portion of solvent 148 to polishing absorber 132'. As the portion of solvent 148 flows downward through polishing absorber 132', the current of gas 146 from within main absorber 14' flows up through polishing absorber 132' in intimate contact with the portion of solvent 148, whereby the portion of solvent 148 absorbs carbon dioxide from the current of gas 146. The current of gas 146 now becomes gas 20a and, in some examples, ultimately becomes gas 20b in cases where propane 126 is added to gas 20a. Gas 20a or 20b can be sold or used as needed.

The portion of solvent 148 after having flowed down through polishing absorber 132', the portion of solvent 148 passes through area of transition 162 to mix with and become part of main current of solvent 150, wherein the main current of solvent 150, including portion 148, flows down through main absorber 14'. In this example, system 158 includes a main solvent loop 168 comprising main absorber 14', line 70, flash system 18, and a return line 170.

As for various methods pertaining to the examples illustrated in FIGS. 1-4, arrow 146 in FIG. 3 provides at least one example of conveying gas through a main absorber. Arrow 146 of FIGS. 1 and 3 provides at least one example of conveying substantially all of the gas from the main absorber through a polishing absorber. Arrow 150 of FIG. 3 provides at least one example of conveying at a main mass flow rate a main current of solvent through the main absorber, thereby exposing the gas to the main current of solvent. An arrow 172 of FIG. 3 provides at least one example of the main current of solvent extracting carbon dioxide from the gas. Arrow 148 of FIG. 1 provides at least one example of conveying at a polishing mass flow rate a polishing current of solvent through the polishing absorber, thereby exposing the gas to the polishing current of solvent. An arrow 174 of FIG. 1 provides at least one example of the polishing current of solvent extracting additional carbon dioxide from the gas. It has been discovered that, in some examples, it appears that having the solvent's main mass flow rate through the main absorber be at least three times greater than the solvent's polishing mass flow rate in the polishing absorber provides surprisingly good results. In some examples, as shown in FIG. 4, the solvent's mass flow rate pertaining to arrow 150 is at least three times greater than the solvent's mass flow rate pertaining to arrow 148. In some examples, as shown in FIGS. 1 and 3, the solvent's mass flow rate pertaining to arrow 150 (FIG. 3) is at least three times greater than the solvent's mass flow rate pertaining to arrow 148 (FIG. 1). FIG. 4 showing absorbers 14' and 132' as a single vessel provides at least one example illustrating housing the main absorber and the polishing absorber within a common outer shell. Transition area 162 between absorbers 14' and 132' provides at least one example illustrating the main absorber and the polishing absorber defining an area of transition therebetween. In FIG. 4, the merging of arrows 148 and 150 provides at least one example illustrating the polishing current of solvent joining and becoming part of the main current of solvent at the area of transition. In FIG. 1, arrow 148 provides at least one example illustrating conveying an ancillary current of solvent through an ancillary absorber. In FIG. 1, an arrow 176 provides at least one example illustrating the ancillary current of solvent flowing from the ancillary absorber to the polishing absorber. In FIG. 1, arrows 148 and 176 provides at least one example illustrating the ancillary current of solvent flowing from the ancillary absorber becoming the polishing current of solvent flowing through the polishing absorber. In FIG. 1, arrow 138 with reference to arrow 148 provides at least one example illustrating conveying a current of air (or nitrogen) through the ancillary absorber, thereby exposing the ancillary current of solvent to the current of air (or nitrogen). An arrow 178 of FIG. 1 provides at least one example illustrating the current of air (or nitrogen) extracting carbon dioxide from the ancillary current of solvent flowing through the ancillary absorber. Arrow 126 of FIG. 1 provides at least one example illustrating adding propane to the gas after the polishing current of solvent extracts additional carbon dioxide from the gas, wherein arrow 174 provides at least one example illustrating extracting additional carbon dioxide from the gas.

In FIG. 3, arrow 180 provide at least one example illustrating circulating a main current of solvent through a main solvent loop. Arrows 146 and 150 of FIG. 3 provides at least one example illustrating exposing the gas to the main current of solvent, thereby reducing the concentration of carbon dioxide in the gas, wherein arrow 172 provides at least one example illustrating reducing the concentration of carbon dioxide in the gas. Arrow 182, shown in FIGS. 2-4, provides at least one example illustrating diverting a portion of solvent from the main solvent loop. Arrows 146, 148 and 174 of FIG. 1 provide at least one example illustrating exposing the gas to the portion of solvent, thereby further reducing the concentration of carbon dioxide in the gas. Arrows 184, 186 and/or 188 of FIG. 3 provide at least one example illustrating decreasing the concentration of carbon dioxide in the main current of solvent to a lower level (e.g. to about 3 mol % carbon dioxide at a point between flash vessel 94 and pump 98), wherein arrows 184, 186 and 188 represent carbon dioxide leaving the main current of solvent. Arrow 178 of FIG. 1 provides at least one example illustrating decreasing the concentration of carbon dioxide in the portion of solvent to less than the lower level (e.g., to about 0.5 mole % carbon dioxide or even less than that, which in either case, is less than 3 mol % carbon dioxide). Arrow 174 of FIG. 1 provides at least one example illustrating increasing the concentration of carbon dioxide in the portion of solvent to an upper level (e.g., 0.6 to 5 mol % carbon dioxide). Arrow 172 of FIG. 3 provides at least one example illustrating increasing the concentration of carbon dioxide in the main current of solvent to greater than the upper level (e.g., to 35 mol % carbon dioxide). Arrows 150 and 180 of FIG. 3 provide at least one example illustrating the main solvent loop passing through the main absorber and the flash system. Arrows 176 and 148 of FIG. 1 provide at least one example illustrating the portion of solvent flowing through the ancillary absorber and the polishing absorber. Arrows 150, 146 and 172 of FIG. 3 provide at least one example illustrating exposing the gas to the main current of solvent and reducing the concentration of carbon dioxide in the gas flowing through the main absorber. Arrows 146, 148 and 174 of FIG. 1 provide at least one example illustrating exposing the gas to the portion of solvent and further reducing the concentration of carbon dioxide in the gas flowing through the polishing absorber. Arrow 188 of FIG. 3 provides at least one example illustrating decreasing the concentration of carbon dioxide in the main current of solvent to the lower level and doing so within the flash system. Arrow 178 of FIG. 1 provides at least one example illustrating decreasing the concentration of carbon dioxide in the portion of solvent to less than the lower level and doing so within the ancillary absorber. Arrow 174 of FIG. 1 provides at least one example illustrating increasing the concentration of carbon dioxide in the portion of solvent to the upper level and doing so within the polishing absorber. Arrow 172 of FIG. 3 provides at least one example illustrating increasing the concentration of carbon dioxide in the main current of solvent to greater than the upper level and doing so within the main absorber. Arrow 142 of FIG. 3 provides at least one example illustrating that after diverting the portion of solvent from the main solvent loop (arrow 182 illustrates diverting the portion), injecting the portion of solvent back into the main solvent loop at a point between the main absorber and the flash system. An arrow 190 of FIG. 4 provides at least one example illustrating that after diverting the portion of solvent from the main solvent loop (e.g., arrow 182 illustrates diverting the portion), injecting the portion of solvent back into the main solvent loop at a point (e.g., transition area 162) between the polishing absorber (e.g., absorber 132') and the main absorber (e.g., absorber 14'). Arrow 142 of FIG. 3 illustrates that after diverting the portion of solvent from the main solvent loop (e.g., arrow 182 illustrates diverting the portion), injecting the portion of solvent back into the main solvent loop at a point (e.g., such injecting being illustrated by arrow 142 of FIG. 3) where the portion of solvent has a concentration of carbon dioxide that is closer to the upper lever (e.g., 2 to 6 mol % carbon dioxide) than to the lower level (e.g., 1 to 3.5 mol % carbon dioxide). Arrows 138, 148 and 178 of FIG. 1 provide at least one example of decreasing the concentration of carbon dioxide in the portion of solvent to less than the lower level and doing so by conveying a current of air in intimate contact with the portion of solvent.

Arrows 148 and 182 and line 140 of FIGS. 1 and 3 provide at least one example illustrating diverting (arrow 182) a portion of solvent from the main solvent loop to create an offshoot solvent path (line 140) conveying an ancillary current of solvent (arrow 148) and a polishing current of solvent (arrow 148), the ancillary current of solvent flowing through an ancillary absorber, the polishing current of solvent flowing through a polishing absorber. Arrow 192 and line 62 of FIGS. 1 and 3 provide at least one example illustrating a pipe conveying the gas from the main shell to the polishing shell. Arrow 142 of FIG. 3 provides at least one example illustrating injecting the portion of solvent back into the main solvent loop at a point downstream of the main absorber and upstream of the flash system.

Figure 5:
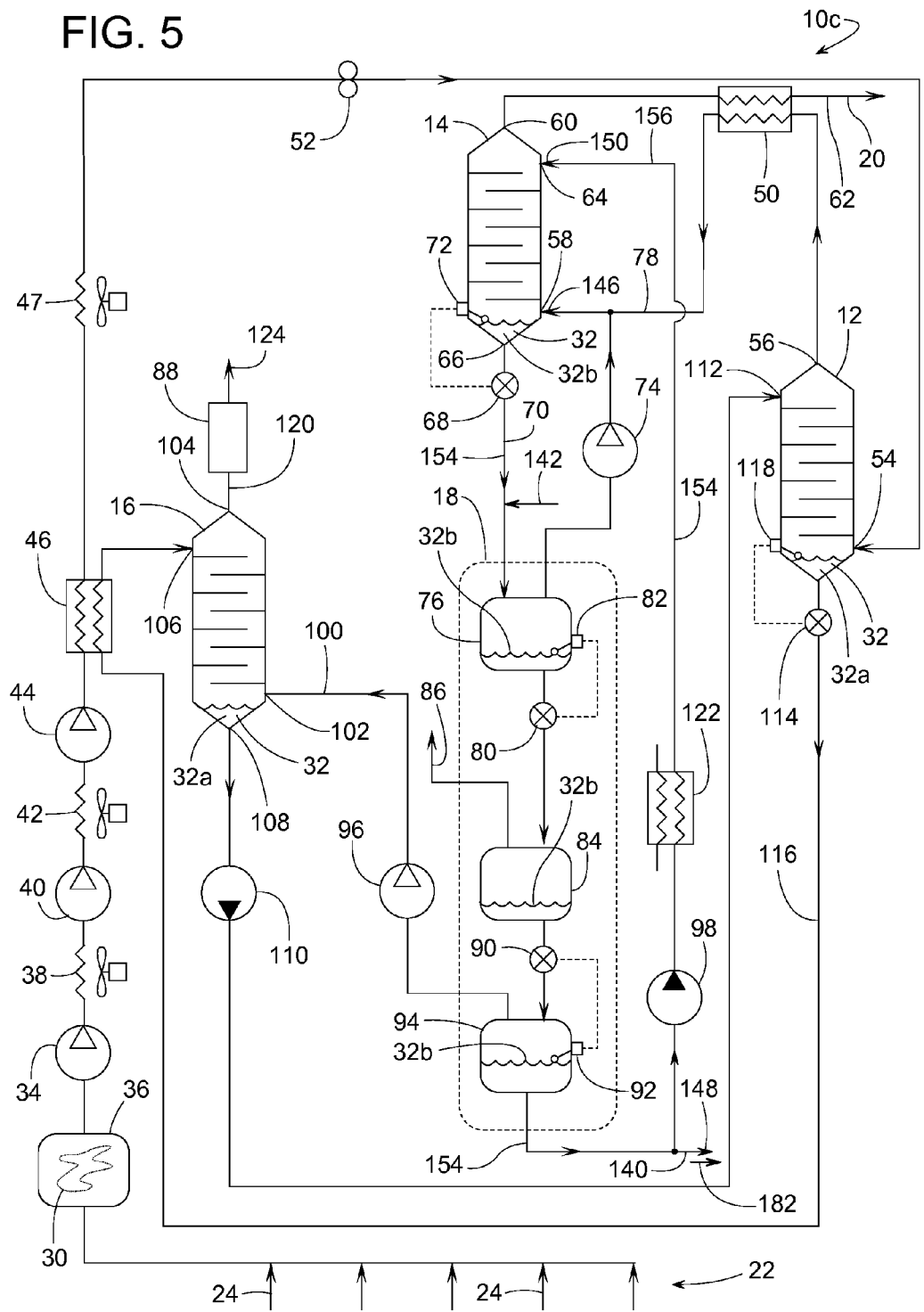
FIG. 5 is a schematic view of another example absorption system connectable to the system shown in FIG. 1.
Figure 6:
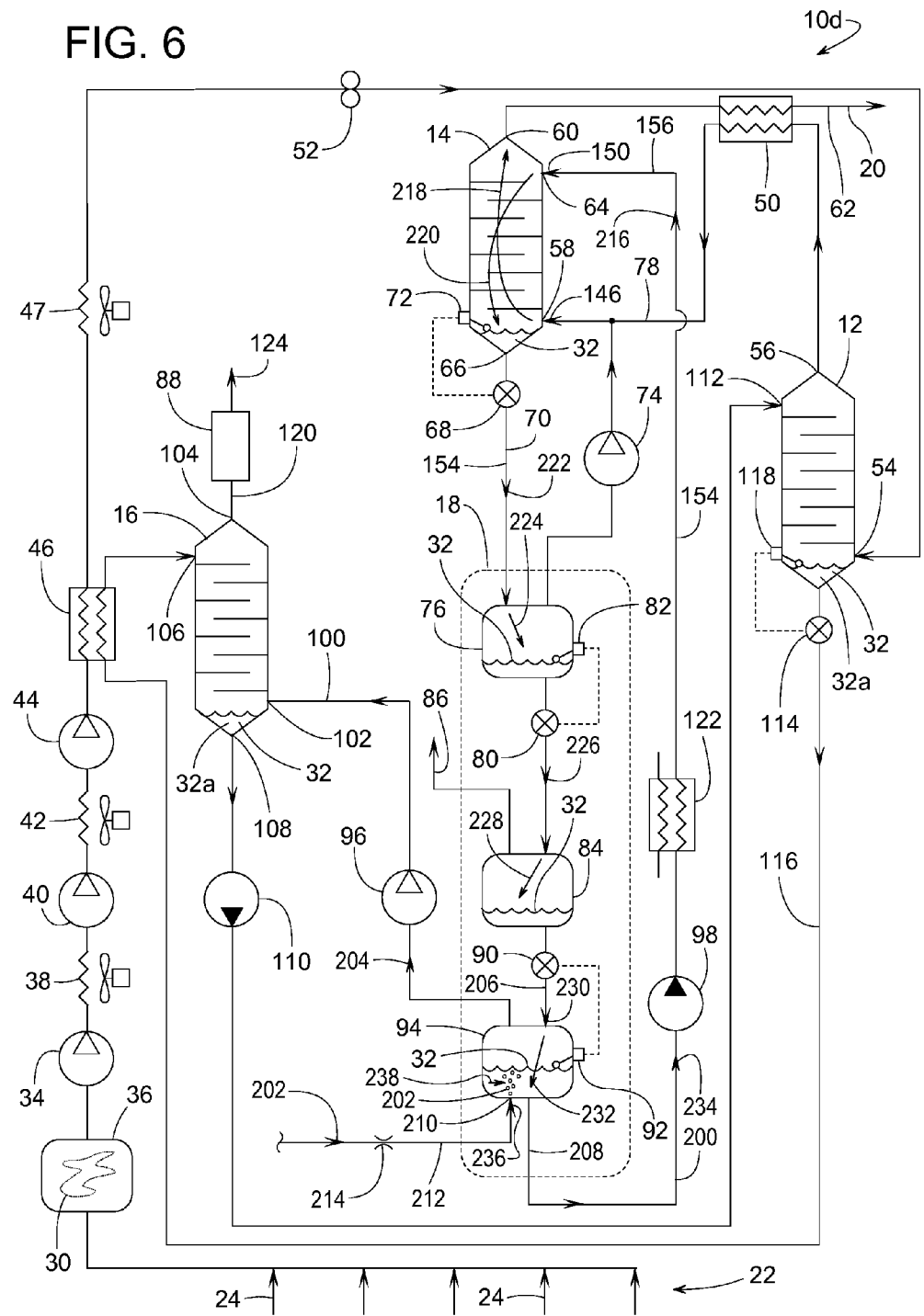
FIG. 6 is a schematic view of another example absorption system and method.
Figure 7:
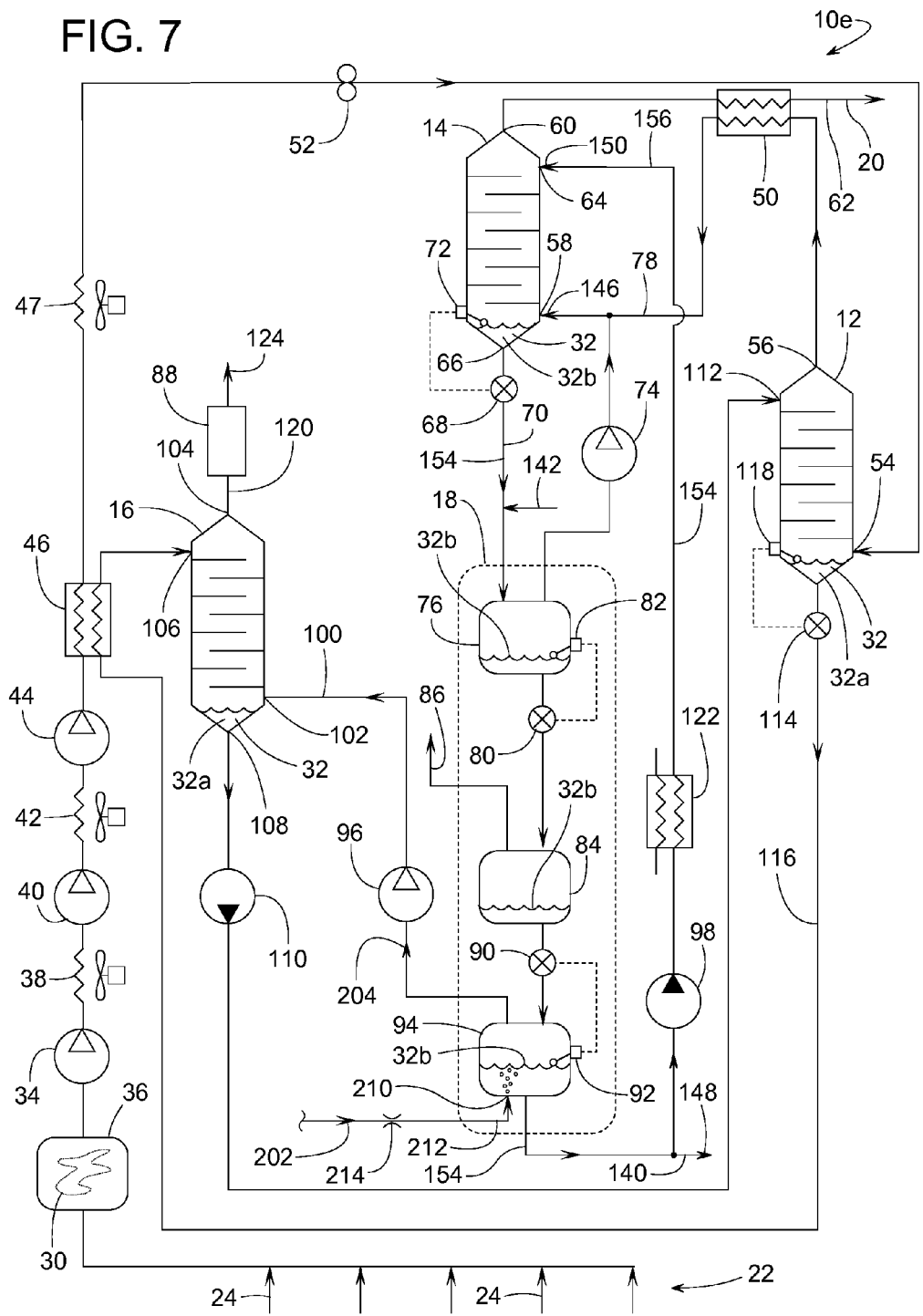
FIG. 7 is a schematic view of another example absorption system connectable to the system shown in FIG. 1.

FIGS. 5, 6 and 7 illustrate example absorption systems 10c, 10d and 10e, respectively, wherein at least portions of absorption systems 10c, 10d and 10e can be used in addition or as an alternative to the examples illustrated in FIGS. 1-3. System 10c of FIG. 5 is similar to system 10a of FIG. 2 with a few exceptions. Instead of conveying recovered gas 30 from heat exchanger 46 through heat exchanger 48 (FIG. 2), recovered gas 30 flows from heat exchanger 46, through a cooler 47 and onto sulfur treater 52. From sulfur treater 52, recovered gas 30 bypasses heat exchanger 50 and flows directly to lower gas inlet 54 of absorber 12. This ensures that recovered gas 30 entering absorber 12 will be at a higher temperature to retard the recovered gas's release of CO2 as gas 30 flows through absorber 12. With the elimination of heat exchanger 48 (FIG. 2), compressor 96 forces the $CO_2$ drawn from flash tank 94 directly into lower gas inlet 102 of third absorber 16, as shown in FIG. 5.

In the examples shown in FIGS. 5-7, gas 30 enters a lower gas inlet 54 of absorber 12 at about 120° F. and 450 psig, travels upward through absorber 12, and exits through an upper gas outlet 56 of absorber 12 at about 450 psig. As gas 30 travels through first absorber 12, first solvent portion 32a travels downward in intimate contact with gas 30 to absorb trace contaminants from gas 30. With most or at least some of the trace contaminants removed, gas 30 enters feed gas to pipeline gas heat exchanger 50 to the lower gas inlet 58 of second absorber 14 at about 75° F. and 450 psig. Also, prior to reaching supply line 62, gas 20 leaving second absorber 14 first passes through heat exchanger 50 to precool gas 30 (flowing to line 78) that is about to enter lower gas inlet 58 of second absorber 14. Precooling gas 30 prior to it entering second absorber 14 promotes the absorption of CO2 from the high $CO_2$ gas stream.

Another difference between system 10c of FIG. 5 and system 10a of FIG. 2 pertains to the use of heat exchanger 50. Heat exchanger 50 when connected as shown in FIG. 5 transfers heat from gas 30 flowing from upper gas outlet 56 to lower gas inlet 58 to gas 30 flowing from sulfur treater 52 to supply line 62.

System 10d of FIG. 6 is similar to system 10c of FIG. 5 but with a few changes. With system 10d, instead of line 140 (FIG. 5) diverting a portion of solvent 148 to ancillary absorber 130 and polishing absorber 132 (FIG. 1) and line 142 returning solvent portion 148 back into the main absorption system, a line 200 conveys solvent 32 directly from flash tank 94 to pump 98. In the example shown in FIG. 6, absorbers 130 and 132 are eliminated. To compensate for the loss of absorbers 130 and 132, a source of stripper gas 202 is injected into third flash tank 94. Examples of stripper gas 202 include, but are not limited to, air, nitrogen, an inert gas, and various mixtures thereof. In some examples, the inert gas for stripping is produced by burning natural gas in air, thereby creating an inert mixture of approximately 79% nitrogen and 21% CO2 (by volume). Stripper gas 202 strips CO2 from solvent 32 in flash tank 94. Stripper gas 202 stripping and collecting CO2 and/or other impurities from solvent 32 within flash tank 94 creates an impure stripper gas 204, which compressor 96 sucks from flash tank 94 and delivers to line 100 leading to lower gas inlet 102 of third absorber 16.

With flash tank 94 being at subatmospheric pressure due to compressor 96 (vacuum pump) and with stripper gas 202, in some examples, being at atmospheric pressure, such a differential between atmospheric and subatmospheric pressure is in itself sufficient for injecting stripper gas 202 into flash tank 94. In some examples, a line 212 conveying stripper gas 202 to flash tank 94 has some flow resistance 214 so that stripper gas 202 can enter line 212 at atmospheric pressure while flash tank 94 can be a subatmospheric pressure. Flow resistance 214 is schematically illustrated to represent any means for resisting flow. Examples of flow resistance 214 include, but are not limited to, line 212 being of a limited diameter, an orifice, a valve, a screen, etc.

Stripper gas 202 can be injected into third flash tank 94 at any injection point (e.g., injection point 210) between a flash tank inlet 206 and a flash tank outlet 208 of flash tank 94. To maximize surface contact and/or mixing between stripper gas 202 and solvent 32, the stripper gas injection point, in some examples, is below the liquid level of solvent 32 in flash tank 94 so that stripper gas 202 bubbles up through a pool of liquid solvent 32. In some examples, to further maximize surface contact and/or promote mixing of stripper gas 202 and solvent 32, flash tank 94 includes mixing baffles, a serpentine flow pattern, a mechanical mixer, a flow distributor and/or some other mixing means.

FIG. 6 also illustrates a method for using solvent 32 in treating recovered gas 30 from landfill 22, wherein gas 30 and solvent 32 have a varying concentration of carbon dioxide. In the method illustrated in FIG. 6, arrow 216 represents conveying the main current of solvent 32 to main absorber 14 that defines upper liquid inlet 64, lower liquid outlet 66, lower gas inlet 58 and upper gas outlet 60. Arrow 218 represents conveying recovered gas 30 through main absorber 14 from lower gas inlet 58 to upper gas outlet 60. Arrow 220 represents conveying the main current of solvent 32 through main absorber 14 from upper liquid inlet 64 to lower liquid outlet 66. Arrow 222 represents conveying the main current of solvent 32 from lower liquid outlet 66 to first flash tank 76. Arrow 224 represents conveying the main current of solvent 32 through first flash tank 76. Arrow 226 represents conveying the main current of solvent 32 from first flash tank 76 to second flash tank 84. Arrow 228 represents conveying the main current of solvent 32 through second flash tank 84. Arrow 230 represents conveying the main current of solvent 32 from second flash tank 84 to third flash tank 94. Arrow 232 represents conveying the main current of solvent 32 through third flash tank 94 from flash tank inlet 206 to flash tank outlet 208 of third flash tank 94. Arrow 234 represents conveying the main current of solvent 32 from flash tank outlet 208 of third flash tank 94 to upper liquid inlet 64 of main absorber 14. The configuration and arrangement of the various components of absorption system 10d, as shown in FIG. 6, illustrates operating third flash tank 94 at subatmospheric pressure, operating second flash tank 84 at a second flash pressure that is greater than the subatmospheric pressure of third flash tank 94, and operating first flash tank 76 at a first flash pressure that is greater than the second flash pressure of second flash tank 84. Arrow 236 represents injecting stripper gas 202 into third flash tank 94 at an injection point that is downstream of flash tank inlet 206 and upstream of the flash tank outlet 208. Arrow 238 represents stripper gas 202 collecting impurities from solvent 32 flowing through third flash tank 94, thereby creating impure stripper gas 204. And compressor 96 represents sucking impure stripper gas 204 at subatmospheric pressure out from within third flash tank 94.

In the example shown in FIG. 7, absorption system 10e is a combination of system 10c (FIG. 5) and system 10d (FIG. 6). Specifically, with system 10e of FIG. 7, solvent 32 is cleaned via stripper gas 202 (FIG. 6) and cleaned via absorbers 130 and 132 (FIGS. 1 and 5).

Additional points worth noting are as follows. Each of the various absorbers mentioned herein (e.g., main absorber, ancillary absorber, polishing absorber) do not necessarily have to be a single vessel but, in some examples, can actually be a group or set of absorber vessels. For instance, in some examples, a main absorber comprises two or more main absorber vessels connected in series or parallel flow relationship with each other. In examples where two absorbers are incorporated within a single vessel, e.g., absorbers 14' and 132' of FIG. 4, a transition area (e.g., area 162) can serve as both a fluid inlet for one absorber and a fluid outlet for the other absorber. For example, area 162 serves as a gas inlet for polishing absorber 132' and a gas outlet for main absorber 14'. Likewise, area 162 serves as a solvent inlet for main absorber 14' and a solvent outlet for polishing absorber 132'. The term, "main solvent loop" means the fluid path along which the solvent circulates through a main absorber and a flash system. The terms, "after" and "following" refer to a flow stream's molecules' experience and not the overall stream's experience. For example, a stream of solvent might flow continuously through two vessels connected in series flow relationship; however, individual molecules in the solvent stream flow through the vessels sequentially, i.e., the molecules flow through one vessel "after" the other, or the molecules flow through a downstream vessel "following" their flowing through an upstream vessel.

Although certain example methods, apparatus and articles of manufacture have been described herein, the scope of the coverage of this patent is not limited thereto. On the contrary, this patent covers all methods, apparatus and articles of manufacture fairly falling within the scope of the appended claims either literally or under the doctrine of equivalents.

The invention claimed is:

1. A method for using a solvent in treating a recovered gas from a landfill, wherein the recovered gas and the solvent have a varying concentration of carbon dioxide, the method comprising:
conveying a main current of solvent to a main absorber that defines an upper liquid inlet, a lower liquid outlet, a lower gas inlet and an upper gas outlet;
conveying the recovered gas through the main absorber from the lower gas inlet to the upper gas outlet;
conveying the main current of solvent through the main absorber from the upper liquid inlet to the lower liquid outlet;
conveying the main current of solvent from the lower liquid outlet to a first flash tank;
conveying the main current of solvent through the first flash tank;
conveying the main current of solvent from the first flash tank to a second flash tank;
conveying the main current of solvent through the second flash tank;
conveying the main current of solvent from the second flash tank to a third flash tank;
conveying the main current of solvent through the third flash tank from a flash tank inlet to a flash tank outlet of the third flash tank;
conveying the main current of solvent from the flash tank outlet of the third flash tank to the upper liquid inlet of the main absorber;
operating the third flash tank at a subatmospheric pressure;
operating the second flash tank at a second flash pressure that is greater than the subatmospheric pressure of the third flash tank;
operating the first flash tank at a first flash pressure that is greater than the second flash pressure of the second flash tank;
injecting a stripper gas into the third flash tank at an injection point that with respect to the solvent flowing through the third flash tank is downstream of the flash tank inlet and upstream of the flash tank outlet;
the stripper gas collecting impurities from the solvent flowing through the third flash tank, thereby creating an impure stripper gas;
sucking the impure stripper gas at subatmospheric pressure out from within the third flash tank;
a first portion of solvent flowing to provide a first current of solvent;
a second portion of solvent flowing to provide the main current of solvent;
the first current of solvent flowing through a first absorber;
the first current of solvent flowing through a third absorber;
the recovered gas flowing through the first absorber; and
the impure stripper gas flowing through the third absorber.

2. The method of claim 1, further comprising the stripper gas flowing at less than atmospheric pressure through the injection point.

3. The method of claim 1, further comprising cooling the main current of solvent flowing from the flash tank outlet of the third flash tank to the upper liquid inlet of the main absorber.

4. The method of claim 1, wherein the stripper gas is mostly air.

5. The method of claim 1, wherein the stripper gas is substantially inert.

6. The method of claim 1, wherein the stripper gas has a greater concentration of nitrogen than that of air.

7. The method of claim 1, wherein the stripper gas comprises a mixture of air and an inert gas.

* * * * *